(12) United States Patent
Tomiyasu et al.

(10) Patent No.: US 10,386,500 B2
(45) Date of Patent: Aug. 20, 2019

(54) IMAGING PANEL AND X-RAY IMAGING DEVICE PROVIDED THEREWITH

(71) Applicant: Sharp Kabushiki Kaisha, Osaka (JP)

(72) Inventors: Kazuhide Tomiyasu, Osaka (JP); Shigeyasu Mori, Osaka (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 420 days.

(21) Appl. No.: 15/321,129

(22) PCT Filed: Jun. 25, 2015

(86) PCT No.: PCT/JP2015/068357
§ 371 (c)(1),
(2) Date: Dec. 21, 2016

(87) PCT Pub. No.: WO2016/002627
PCT Pub. Date: Jan. 7, 2016

(65) Prior Publication Data
US 2017/0131413 A1    May 11, 2017

(30) Foreign Application Priority Data

Jun. 30, 2014   (JP) ................................. 2014-134752

(51) Int. Cl.
*G01T 1/20* (2006.01)
*G01T 1/24* (2006.01)
(Continued)

(52) U.S. Cl.
CPC ............... *G01T 1/20* (2013.01); *G01N 23/04* (2013.01); *G01T 1/247* (2013.01); *H01L 27/144* (2013.01);
(Continued)

(58) Field of Classification Search
CPC .......... H01L 2/14692; H01L 27/14694; H01L 27/14696; H01L 27/14603;
(Continued)

(56) References Cited

U.S. PATENT DOCUMENTS

2004/0104351 A1   6/2004  Shibayama
2009/0057564 A1   3/2009  Miyayama et al.
(Continued)

FOREIGN PATENT DOCUMENTS

JP    2002-124676 A    4/2002
JP    2006-156555 A    6/2006
(Continued)

OTHER PUBLICATIONS

U.S. Appl. No. 15/320,682, filed Dec. 20, 2016.
(Continued)

*Primary Examiner* — Don K Wong
(74) *Attorney, Agent, or Firm* — ScienBiziP, P.C.

(57) ABSTRACT

Provided is a technique that reduces patterning defects of data lines in an imaging panel and drain electrodes in thin film transistors without lowering the aperture ratio of the imaging panel. The imaging panel captures scintillation light, which are X-rays that have passed through a specimen and been converted by a scintillator. The imaging panel includes a plurality of gate lines and a plurality of data lines. The imaging panel includes, in each of the pixels, a conversion element that converts scintillation light to electric charge, and a thin film transistor connected to the gate line, data line, and conversion element. A drain electrode of the thin film transistor is formed such that edges of the drain electrode near the data line are more inside the pixel than edges of the conversion element near the data line.

6 Claims, 7 Drawing Sheets

(51) Int. Cl.

| | | |
|---|---|---|
| *H01L 31/0216* | (2014.01) | |
| *H01L 31/18* | (2006.01) | |
| *H01L 27/144* | (2006.01) | |
| *H01L 27/146* | (2006.01) | |
| *H01L 31/10* | (2006.01) | |
| *H04N 5/32* | (2006.01) | |
| *G01N 23/04* | (2018.01) | |
| *H01L 29/04* | (2006.01) | |
| *H01L 29/786* | (2006.01) | |
| *A61B 6/00* | (2006.01) | |

(52) U.S. Cl.
CPC ...... *H01L 27/146* (2013.01); *H01L 27/14612* (2013.01); *H01L 27/14636* (2013.01); *H01L 27/14663* (2013.01); *H01L 29/04* (2013.01); *H01L 29/7869* (2013.01); *H01L 31/10* (2013.01); *H04N 5/32* (2013.01); *A61B 6/4208* (2013.01)

(58) Field of Classification Search
CPC ......... H01L 27/14601; H01L 27/14663; H01L 27/14609; H01L 27/14632
See application file for complete search history.

(56) References Cited

U.S. PATENT DOCUMENTS

| | | |
|---|---|---|
| 2009/0078877 A1 | 3/2009 | Yaegashi et al. |
| 2009/0250699 A1 | 10/2009 | Okada |
| 2011/0127593 A1* | 6/2011 | Hayashi ............. H01L 27/1461 257/292 |
| 2011/0133095 A1 | 6/2011 | Imai |
| 2011/0186853 A1 | 8/2011 | Terai et al. |
| 2012/0313103 A1 | 12/2012 | Yamada et al. |
| 2013/0264485 A1 | 10/2013 | Kawanabe et al. |
| 2013/0299711 A1 | 11/2013 | Mochizuki et al. |
| 2013/0307041 A1 | 11/2013 | Mochizuki et al. |
| 2014/0103347 A1 | 4/2014 | Ishino |
| 2017/0139056 A1 | 5/2017 | Tomiyasu et al. |
| 2017/0148843 A1 | 5/2017 | Mori et al. |
| 2017/0154914 A1 | 6/2017 | Tomiyasu et al. |
| 2017/0154915 A1 | 6/2017 | Tomiyasu et al. |
| 2017/0154916 A1 | 6/2017 | Mori et al. |
| 2017/0160403 A1 | 6/2017 | Tomiyasu et al. |

FOREIGN PATENT DOCUMENTS

| | | |
|---|---|---|
| JP | 2006-253481 A | 9/2006 |
| JP | 2007-103578 A | 4/2007 |
| JP | 2009-59975 A | 3/2009 |
| JP | 2009-94465 A | 4/2009 |
| JP | 2009-212120 A | 9/2009 |
| JP | 2009-252835 A | 10/2009 |
| JP | 2010-98329 A | 4/2010 |
| JP | 2011-124334 A | 6/2011 |
| JP | 2011-159908 A | 8/2011 |
| JP | 2013-16772 A | 1/2013 |
| JP | 2013-219067 A | 10/2013 |
| JP | 2013-235934 A | 11/2013 |
| JP | 2013-235935 A | 11/2013 |

OTHER PUBLICATIONS

U.S. Appl. No. 15/320,704, filed Dec. 20, 2016.
U.S. Appl. No. 15/321,132, filed Dec. 21, 2016.
U.S. Appl. No. 15/321,142, filed Dec. 21, 2016.
U.S. Appl. No. 15/321,127, filed Dec. 21, 2016.
U.S. Appl. No. 15/320,712, filed Dec. 20, 2016.
English translation of JP 2009-094465. (Listed by the U.S. Examiner in a PTO-892 form in the related U.S. Appl. No. 15/320,682.).

* cited by examiner

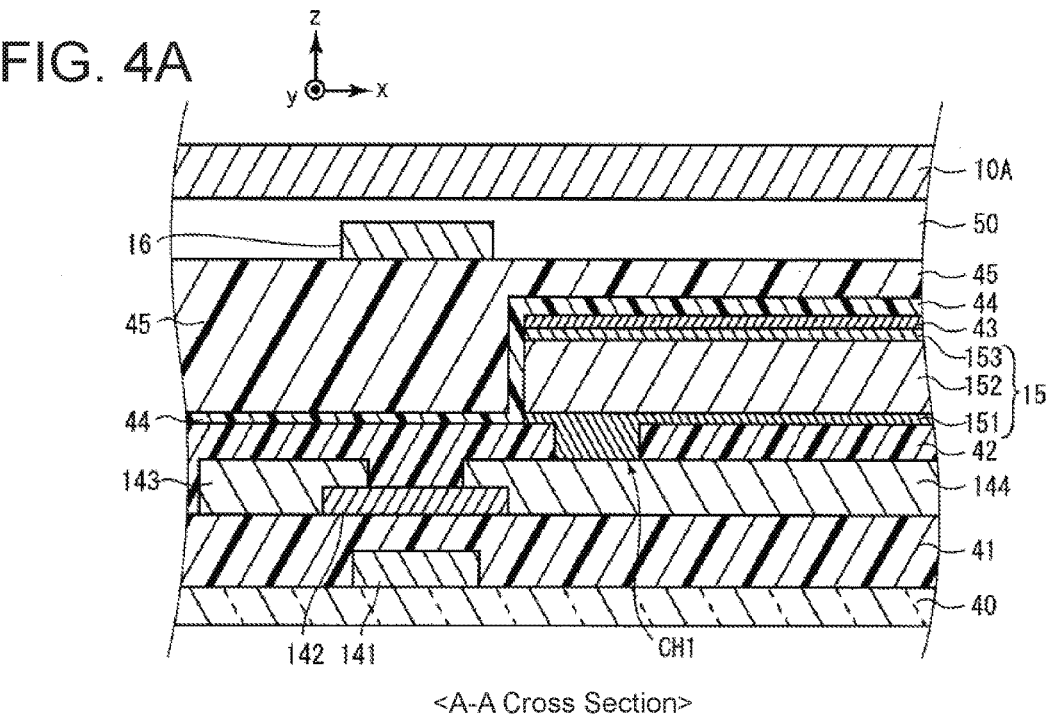
FIG. 4A  <A-A Cross Section>
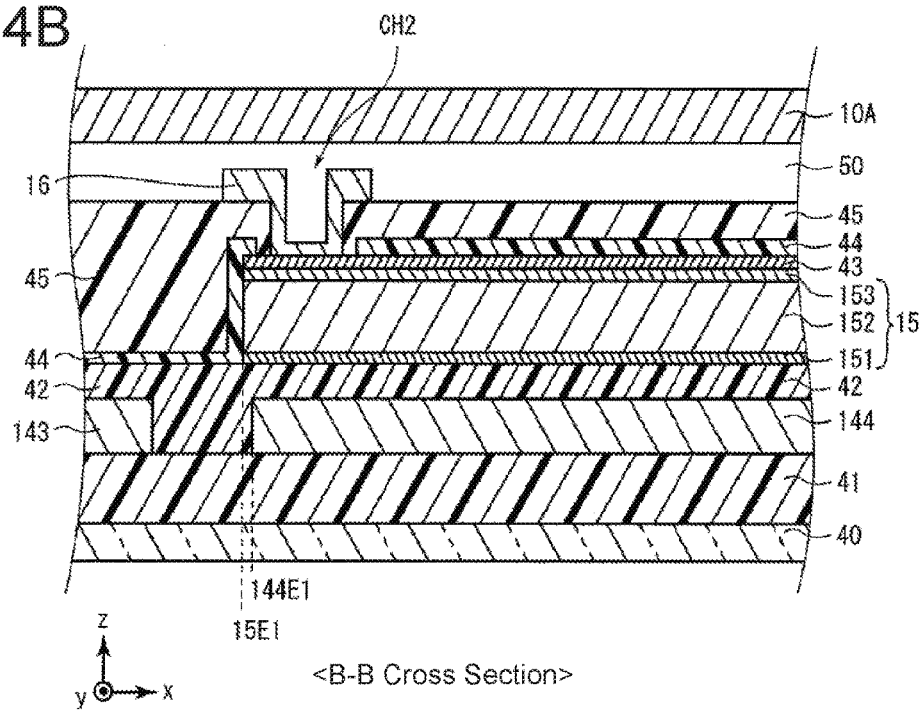
FIG. 4B  <B-B Cross Section>

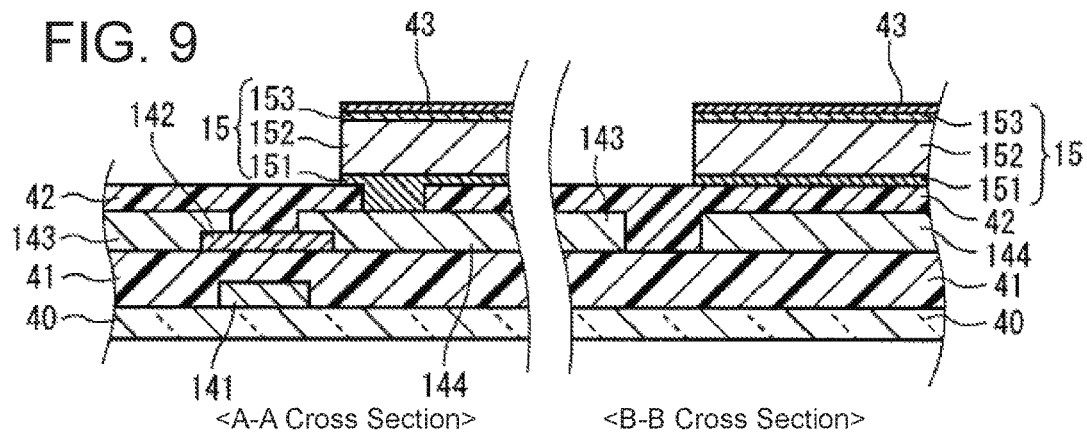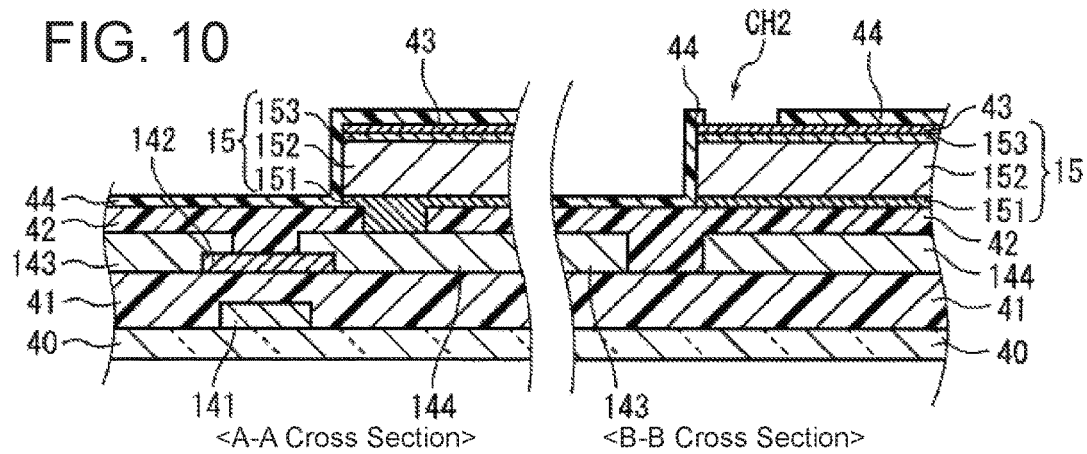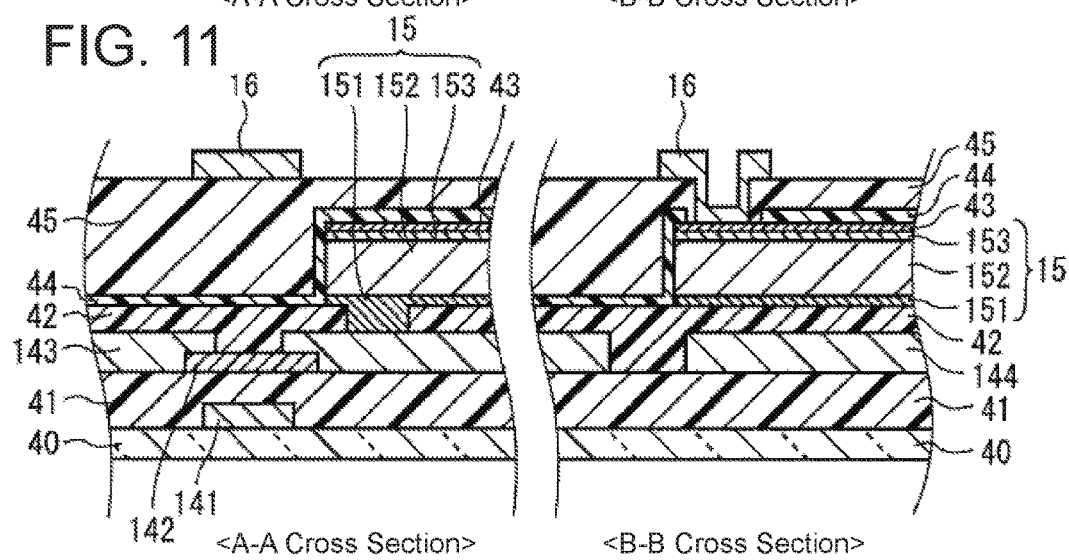

<A-A Cross Section>

<A-A Cross Section>

US 10,386,500 B2

IMAGING PANEL AND X-RAY IMAGING DEVICE PROVIDED THEREWITH

TECHNICAL FIELD

The present invention relates to an imaging panel and an X-ray imaging device provided therewith.

BACKGROUND ART

There are X-ray imaging devices that take X-ray images via an imaging panel having a plurality of pixels. Japanese Patent Application Laid-Open Publication No. 2002-124676 discloses a technique whereby each pixel has a thin film transistor (TFT) and a photodiode, and X-rays passing through a specimen are converted to fluorescent light and then converted to electric charge by the photodiode, with the charge stored in the pixel being read out by operating the TFT. The drain electrode of the thin film transistor has a larger area than the photodiode and is disposed in the vicinity of the data line.

SUMMARY OF THE INVENTION

The larger that the area of the photodiode is, the higher that the definition and resolution of the image can be. However, the larger the area of the photodiode, the narrower the gaps between the elements formed in the same layer as the pixels. In particular, the drain electrode of the thin film transistor and the data line are formed in the same layer, and thus the narrower the gaps between these elements are, the more susceptibility to pattern defects there are if particles attach between these elements in the manufacturing process.

The present invention aims at providing a technique to reduce patterning defects of the data line of the imaging panel and the drain electrode of the thin film transistor without lowering the aperture ratio of the imaging panel.

An imaging panel of the present invention is an imaging panel for capturing scintillation light that has been converted by a scintillator from X-rays radiated from an X-ray source, the imaging panel including: a substrate; a plurality of gate lines on the substrate; a plurality of data lines on the substrate and intersecting the plurality of gate lines; a plurality of conversion elements respectively disposed in a plurality of regions demarcated by the plurality of gate lines and the plurality of data lines, the plurality of conversion elements receiving the scintillation light and converting the scintillation light to electric charge; and thin film transistors respectively disposed in the plurality of regions and connected to the conversion element in the corresponding region and connected to the gate line and the data line contacting the corresponding region, each of the thin film transistors including a drain electrode in a same layer as the data line, and having a semiconductor active layer therein, and, in each of the plurality of regions, an edge of the drain electrode near the data line is more inside the corresponding region than an edge of the conversion element near the data line.

The present invention makes it possible to reduce patterning defects of the data line of the imaging panel and the drain electrode of the thin film transistor without lowering the aperture ratio of the imaging panel.

BRIEF DESCRIPTION OF THE DRAWINGS

FIG. 4A is a cross-sectional view of FIG. 3 along the line A-A.

FIG. 4B is a cross-sectional view of FIG. 3 along the line B-B.

FIG. 9 is a cross-sectional view during a manufacturing process of a photodiode of the pixel shown in FIG. 3 along the line A-A and along the line B-B.

FIG. 10 is a cross-sectional view during a manufacturing process of an interlayer insulating film of the pixel shown in FIG. 3 along the line A-A and along the line B-B.

FIG. 11 is a cross-sectional view during a manufacturing process of a photosensitive resin layer and bias wiring line of the pixel shown in FIG. 3 along the line A-A and along the line B-B.

DETAILED DESCRIPTION OF EMBODIMENTS

Figure 1:
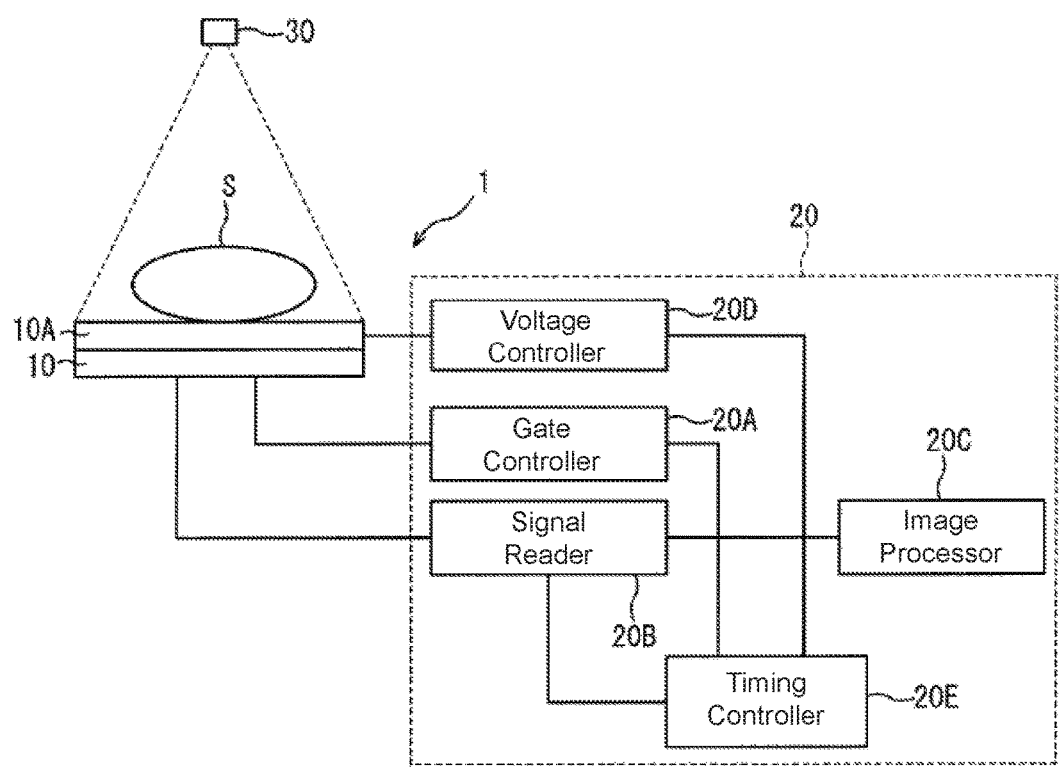
FIG. 1 is a schematic diagram showing an X-ray imaging device of an embodiment.

An imaging panel of one embodiment of the present invention is an imaging panel for capturing scintillation light that has been converted by a scintillator from X-rays radiated from an X-ray source, the imaging panel including: a substrate; a plurality of gate lines on the substrate; a plurality of data lines on the substrate and intersecting the plurality of gate lines; a plurality of conversion elements respectively disposed in a plurality of regions demarcated by the plurality of gate lines and the plurality of data lines, the plurality of conversion elements receiving the scintillation light and converting the scintillation light to electric charge; and thin film transistors respectively disposed in the plurality of regions and connected to the conversion element in the corresponding region and connected to the gate line and the data line contacting the corresponding region, each of the thin film transistors including a drain electrode in a same layer as the data line, and having a semiconductor active layer therein, and, in each of the plurality of regions, an edge of the drain electrode near the data line is more inside the corresponding region than an edge of the conversion element near the data line (first configuration).

According to the first configuration, the edges near the data line of the drain electrode in the thin film transistor, which is disposed in a region demarcated by gate lines and data lines, are more inside the region than the edges of the conversion element near the data line. Thus, the gap between the data line and drain electrode is better than if the respective edges of the conversion element and drain electrode near the data line were at approximately the same location. Accordingly, when forming the conversion element up to an area approximate to the data line in order to increase the aperture ratio, it is harder for pattern defects to occur in the data line and drain electrode, even if particles become attached between the data line and drain electrode.

A second configuration is the first configuration, in which the semiconductor active layer may be made of an oxide semiconductor.

A third configuration is the first configuration, in which the semiconductor active layer may be amorphous silicon or polycrystalline silicon.

A fourth configuration is any one of the first to third configurations, in which the thin film transistors may each include: a gate electrode on the substrate; an insulating film covering the gate electrode; and a source electrode on the insulating film and connected to the semiconductor active layer, and the drain electrode may be on the insulating film and connected to the semiconductor active layer, and the semiconductor active layer may be on the insulating film.

A fifth configuration is any one of the first to third configurations, in which the thin film transistors may each include: a source electrode connected to the semiconductor active layer; an insulating film covering the semiconductor active layer, the source electrode, and the drain electrode; and a gate electrode on the insulating film, and the drain electrode may be connected to the semiconductor active layer.

An X-ray imaging device of one embodiment of the present invention the imaging panel according to any one of the first to fifth configurations, a controller controlling gate voltages of the thin film transistors in the imaging panel and reading out via the data lines data voltages that correspond to electric charge converted by the conversion elements; an X-ray light source radiating X-rays; and a scintillator converting the X-rays to scintillation light (sixth configuration).

Embodiments of the present invention will be described in detail below with reference to the drawings. Portions in the drawings that are the same or similar are assigned the same reference characters and descriptions thereof will not be repeated.

(Configuration)

FIG. 1 is a schematic diagram showing an X-ray imaging device of an embodiment. An X-ray imaging device 1 includes an imaging panel 10, scintillator 10A, controller 20, and X-ray light source 30. X-rays from the X-ray light source 30 irradiate a specimen S, and the X-rays that have passed through the specimen S are converted to fluorescent light (hereinafter, scintillator light) by the scintillator 10A at the top of the imaging panel 10. The X-ray imaging device 1 captures X-ray images by the scintillator light being imaged by the imaging panel 10 and the controller 20.

Figure 2:
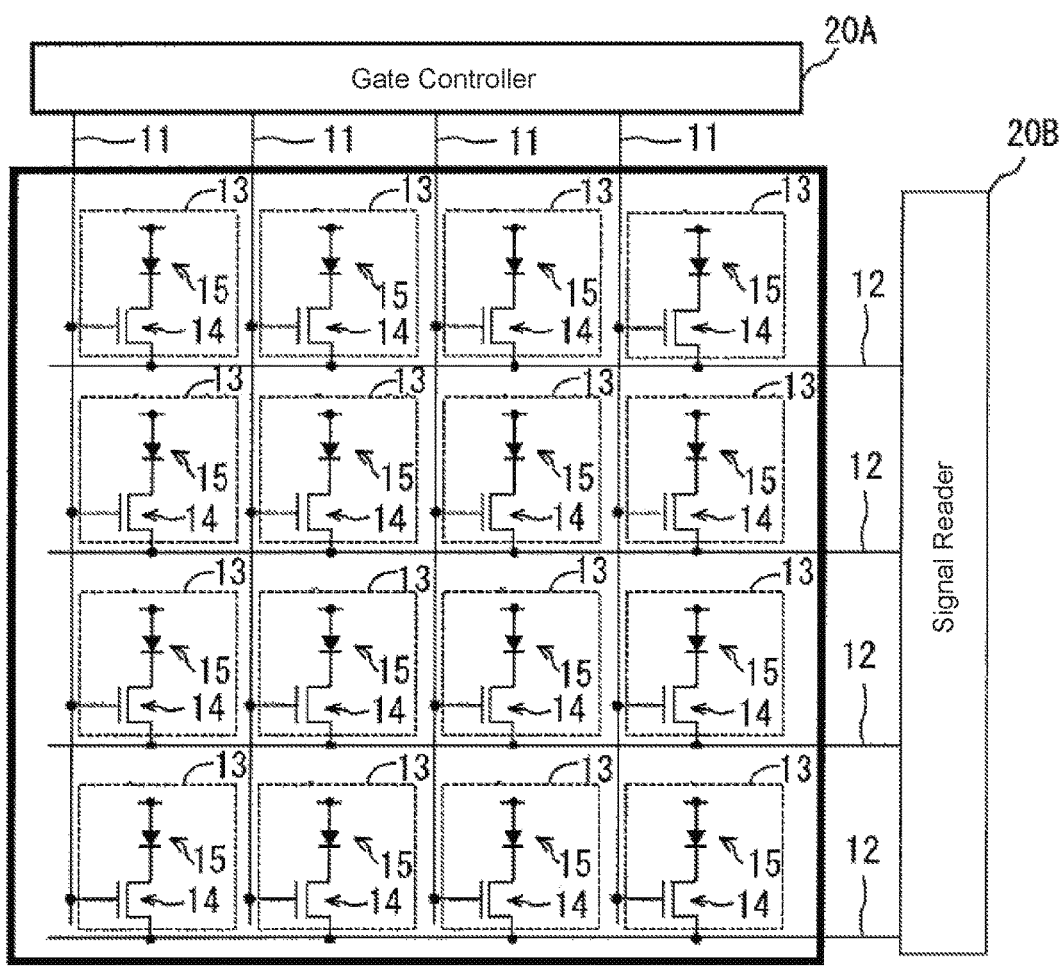
FIG. 2 is a schematic diagram showing a general configuration of the imaging panel in FIG. 1.

FIG. 2 is a schematic diagram showing a general configuration of the imaging panel 10. As shown in FIG. 2, a plurality of gate lines 11 and a plurality of data lines 12 intersecting the plurality of gate lines 11 are formed on the imaging panel 10. The imaging panel 10 has a plurality of pixels 13 defined by the gate lines 11 and data lines 12. FIG. 2 shows an example that has 16 (4×4) pixels 13, but the number of pixels in the imaging panel 10 is not limited to this.

Each of the pixels 13 has a thin film transistor (TFT) 14 connected to the gate line 11 and data line 12, and a photodiode 15 connected to the TFT 14. Furthermore, while not shown in FIG. 2, each of the pixels 13 has a bias line 16 (see FIG. 3) that supplies bias voltage to the photodiode 15, and this bias line is disposed roughly parallel to the data line 12.

In each of the pixels 13, the scintillation light, or namely the converted X-rays that have passed through the specimen S, is converted by the photodiode 15 into an electric charge that corresponds to the intensity of scintillation light.

Each of the gate lines 11 in the imaging panel 10 is switched to a sequentially selectable state by the gate line controller 20A, and the TFT 14 connected to the gate line 11 in the selected state turns ON. When the TFT 14 turns ON, a data signal corresponding to the electric charge converted by the photodiode 15 is output via the data line 12.

Figure 3:
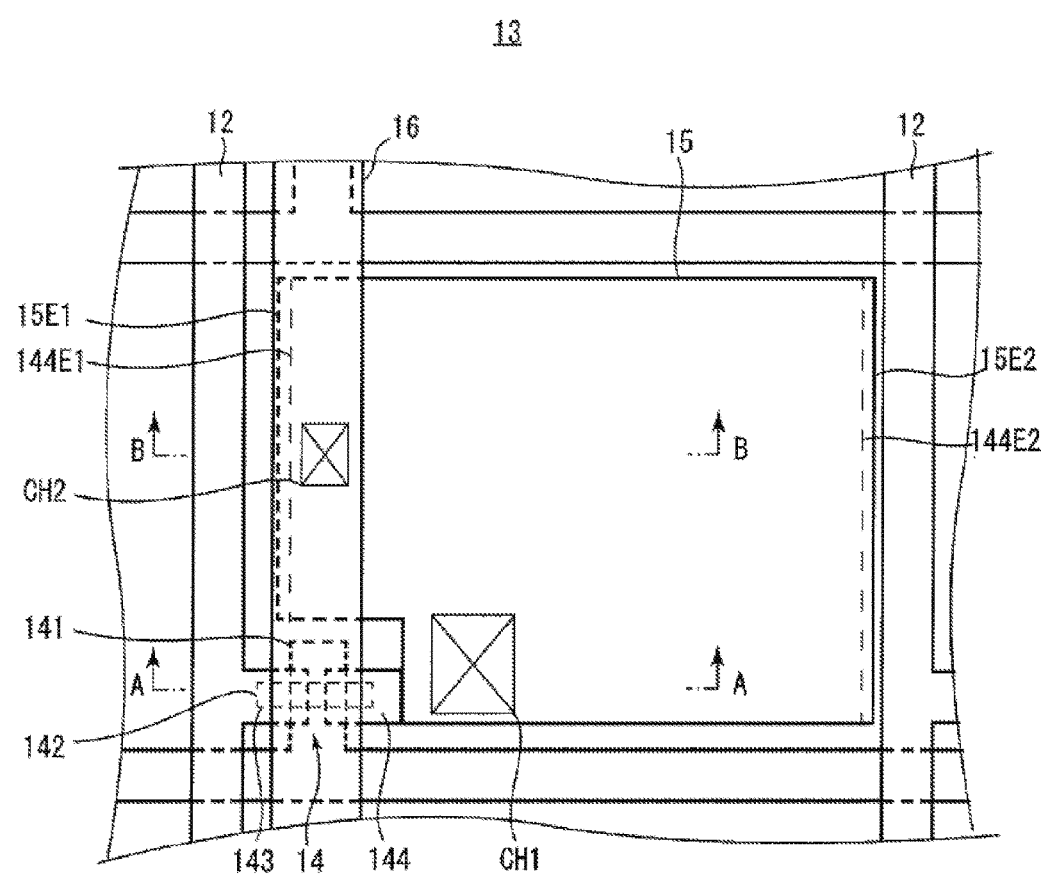
FIG. 3 is a plan view of a pixel from the imaging panel in FIG. 2.

Next, a specific configuration of the pixel 13 will be described. FIG. 3 is a plan view of the pixel 13 from the imaging panel 10 shown in FIG. 2. FIG. 4A is a cross-sectional view of the pixel 13 shown in FIG. 3 along the line A-A, and FIG. 4B is a cross-sectional view of the pixel 13 shown in FIG. 3 along the line B-B.

As shown in FIG. 4A and FIG. 4B, the pixel 13 is formed on a substrate 40. The substrate 40 is an insulating substrate such as a glass substrate, silicon substrate, a heat-resistant plastic substrate, a resin substrate, or the like, for example. In particular, for a plastic substrate or resin substrate, polyethyleneterephthalate (PET), polyethylene naphthalate (PEN), polyethersulfone (PES), acrylic, polyimide, or the like may be used.

The TFT 14 includes a gate electrode 141, semiconductor active layer 142 disposed on the gate electrode 141 with a gate insulating film 41 therebetween, and a source electrode 143 and drain electrode 144 connected to the semiconductor active layer 142.

The gate electrode 141 is formed contacting one surface (hereinafter, main surface) of the substrate 40 in the thickness direction. The gate electrode 141 is made of a metal such as aluminum (Al), tungsten (W), molybdenum (Mo), tantalum (Ta), chromium (Cr), titanium (Ti), or copper (Cu), or is an alloy of these metals or a metal nitride of these, for example. The gate electrode 141 may also be constituted by a plurality of metal films layered together, for example. In the present embodiment, the gate electrode 141 has a layered structure in which an aluminum metal film and titanium metal film are layered together in this order.

As shown in FIG. 4A, the gate insulating film 41 is formed on the substrate 40 and covers the gate electrode 141. The gate insulating film 41 may be silicon oxide (SiOx), silicon nitride (SiNx), silicon oxynitride (SiOxNy) (x>y), silicon nitrogen oxide (SiNxOy) (x>y), or the like, for example.

In order to prevent diffusion of impurities or the like from the substrate 40, the gate insulating film 41 may be a multilayer structure. For example, the lower layer may be silicon nitride (SiNx), silicon nitrogen oxide (SiNxOy) (x>y), etc., and the upper layer may be silicon oxide (SiOx), silicon oxynitride (SiOxNy) (x>y), etc. Moreover, in order to form a compact gate insulating film that has little gate leakage current at low formation temperatures, a noble gas such as argon may be included in the reactive gas so as to be mixed into the insulating film. In the present embodiment, the gate insulating film 41 has a multilayer structure in which the bottom layer is a 100 nm-400 nm silicon nitride film formed with a reactant gas of $SiH_4$ and $NH_3$, and the top layer is a 50 nm-100 nm silicon oxide film.

As shown in FIG. 4A, the semiconductor active layer 142 is formed contacting the gate insulating film 41. The semiconductor active layer 142 is an oxide semiconductor. The oxide semiconductor may be an amorphous oxide semiconductor or the like containing InGaO$_3$ (ZnO)$_5$, magnesium zinc oxide (MgxZn$_1$-xO), cadmium zinc oxide (CdxZn$_1$-xO), cadmium oxide (CdO), or containing prescribed proportions of indium (In), gallium (Ga), and zinc (Zn), for example. The semiconductor active layer 142 may be a ZnO amorphous material doped with one or more impurity elements selected among group 1 elements, group 13 elements, group 14 elements, group 15 elements, group 17 elements, and the like, or a polycrystalline material. Alternatively, the semiconductor active layer be a microcrystalline material (a mix of amorphous and polycrystalline states), or a material that has had no impurities added.

As shown in FIG. 4A and FIG. 4B, the source electrode 143 and drain electrode 144 are formed contacting the semiconductor active layer 142 and the gate insulating film 41. As shown in FIG. 3, the source electrode 143 is connected to the data line 12, and the drain electrode 144 is connected to the photodiode 15 via a contact hole CH1. The source electrode 143, data line 12, and drain electrode 144 are formed on the same layer.

The source electrode 143, data line 12, and drain electrode 144 are made of a metal such as aluminum (Al), tungsten (W), molybdenum (Mo), tantalum (Ta), chromium (Cr), titanium (Ti), or copper (Cu), or are an alloy of these metals or a metal nitride of these, for example. Alternatively, the source electrode 143, data line 12, and drain electrode 144 may be a transmissive material such as indium tin oxide (ITO), indium zinc oxide (IZO), indium tin oxide containing silicon oxide (ITSO), indium oxide (In$_2$O$_3$), tin oxide (SnO$_2$), zinc oxide (ZnO), titanium nitride, or the like, or may be a combination of these.

The source electrode 143, data line 12, and drain electrode 144 may be constituted by a plurality of metal films layered together, for example. In the present embodiment, the source electrode 143, data line 12, and drain electrode 144 have a multilayer structure in which a titanium metal film, aluminum metal film, and titanium metal film are layered together in this order.

As shown in FIG. 4A and FIG. 4B, the interlayer insulating film 42 covers the semiconductor active layer 142, source electrode 143, data line 12, and drain electrode 144. The interlayer insulating film 42 may be a single layer structure made of silicon oxide (SiO$_2$) or silicon nitride (SiN), or a multilayer structure in which silicon nitride (SiN) and silicon oxide (SiO$_2$) are layered together in this order.

As shown in FIG. 4A and FIG. 4B, the photodiode 15 is formed on the interlayer insulating film 42 contacting the drain electrode 144. The photodiode 15 includes an n-type amorphous silicon layer 151, an intrinsic amorphous silicon layer 152, and a p-type amorphous silicon layer 153.

The n-type amorphous silicon layer 151 is made of amorphous silicon that has been doped with an n-type impurity (phosphorous, for example). The n-type amorphous silicon layer 151 is formed contacting the drain electrode 144. The thickness of the n-type amorphous silicon layer 151 is 20 nm to 100 nm, for example.

The intrinsic amorphous silicon layer 152 is made of intrinsic amorphous silicon. The intrinsic amorphous silicon layer 152 is formed contacting the n-type amorphous silicon layer 151. The thickness of the intrinsic amorphous silicon layer is 200 nm to 2000 nm, for example.

The p-type amorphous silicon layer 153 is made of amorphous silicon that has been doped with a p-type impurity (boron, for example). The p-type amorphous silicon layer 153 is formed contacting the intrinsic amorphous silicon layer 152. The thickness of the p-type amorphous silicon layer 153 is 10 nm to 50 nm, for example.

As shown in FIG. 3 and FIG. 4B, in the present embodiment, the drain electrode 144 in the pixel 13 is formed such that the edge of the drain electrode 144 near the data line 12 is more inside the pixel 13 than the edge of the photodiode 15 near the data line 12. More specifically, edge portions 144E1 and 144E2 of the drain electrode 144 in the extension direction of the gate line 11 and not connected to the semiconductor active layer 142 are more inside the pixel 13 (in the positive X-axis direction) than edge portions 15E1 and 15E2 of the photodiode 15 in the extension direction of the gate line 11. The drain electrode 144 functions as the drain electrode of the TFT 14 and the bottom electrode of the photodiode 15. Furthermore, the drain electrode 144 also functions as a reflective film that reflects scintillation light that has passed through the photodiode 15 back toward the photodiode 15.

As shown in FIG. 4A and FIG. 4B, an electrode 43 is formed on top of the photodiode 15 and functions as the top electrode of the photodiode 15. The electrode 43 is made of indium zinc oxide (IZO), for example.

An interlayer insulating film 44 is formed contacting the interlayer insulating film 42 and electrode 43. The interlayer insulating film 44 may be a single layer structure made of silicon oxide (SiO$_2$) or silicon nitride (SiN), or a multilayer structure in which silicon nitride (SiN) and silicon oxide (SiO$_2$) are layered together in this order.

A photosensitive resin layer 45 is formed on top of the interlayer insulating film 44. The photosensitive resin layer 45 is made of an organic resin material or an inorganic resin material.

As shown in FIGS. 3, 4A, and 4B, the bias wiring line 16 is formed on the photosensitive resin layer 45 substantially parallel to the data line 12. Specifically, as shown in FIGS. 4A and 4B, the bias wiring line 16 is formed on top of the photosensitive resin layer 45 so as to overlap the TFT 14. Furthermore, as shown in FIG. 4B, the bias wiring line 16 is formed so as to overlap the edge portion 15E1 of the photodiode 15 near the data line 12 to which the TFT 14 is connected. The bias wiring line 16 is connected to a voltage controller 20D (see FIG. 1). As shown in FIG. 4B, the bias wiring line 16 is connected to the electrode 43 via a contact hole CH2, and bias voltage received from the voltage controller 20 is applied to the electrode 43. The bias wiring line 16 has a multilayer structure in which indium zinc oxide (IZO) and molybdenum (Mo) are layered together, for example.

As shown in FIGS. 4A and 4B, a protective layer 50 is formed on top of the imaging panel 10, or namely on top of the photosensitive resin layer 45, so as to cover the bias wiring line 16, and the scintillator 10A is disposed on top of the protective layer 50.

The configuration of the controller 20 will be explained while referring back to FIG. 1. The controller 20 includes a gate controller 20A, signal reader 20B, image processor 20C, voltage controller 20D, and timing controller 20E.

As shown in FIG. 2, the gate controller 20A is connected to a plurality of the gate lines 11. The gate controller 20A applies, via the gate lines 11, a prescribed gate voltage to the TFTs 14 of the pixels 13 connected to the gate lines 11.

As shown in FIG. 2, the signal reader 20B is connected to the plurality of data lines 12. The signal reader 20B, via the respective data lines 12, reads out data signals that correspond to the electric charge converted by the photodiode 15 of the pixel 13. The signal reader 20B generates image signals based on the data signals and outputs the result to the image processor 20C.

The image processor 20C generates X-ray images based on the image signals output from the signal reader 20B.

The voltage controller 20D is connected to the bias wiring line 16. The voltage controller 20D applies a prescribed bias voltage to the bias wiring line 16. This applies a bias voltage to the photodiode 15 via the electrode 43 connected to the bias wiring line 16.

The timing controller 20E controls the operation timing of the gate controller 20A, signal reader 20B, and voltage controller 20D.

The gate controller 20A selects one gate line 11 from the plurality of gate lines 11 based on the control signal from the timing controller 20E. The gate controller 20A applies, via the selected gate line 11, a prescribed gate voltage to the TFT 14 of the pixel 13 connected to the corresponding gate line 11.

The signal reader 20B selects one data line 12 from the plurality of data lines 12 based on the control signal from the timing controller 20E. The signal reader 20B, via the selected data line 12, reads out the data signal corresponding to the electric charge converted by the photodiode 15 of the pixel 13. The pixel 13 where the data signal has been read out is connected to the data line 12 selected by the signal reader 20B and connected to the gate line 11 selected by the gate controller 20A.

When irradiated by X-rays from the X-ray light source 30, the timing controller 20E outputs a control signal to the voltage controller 20D, for example. Based on this control signal, the voltage controller 20D applies a prescribed bias voltage to the electrode 43.

(Operation of X-Ray Imaging Device 1)

First, X-rays are radiated from the X-ray light source 30. At such time, the timing controller 20E outputs a control signal to the voltage controller 20D. Specifically, a signal indicating that X-rays have been radiated from the X-ray light source 30 is output from a controller that controls operation of the X-ray light source 30 to the timing controller 20E, for example. When this signal has been received by the timing controller 20E, the timing controller 20E outputs a control signal to the voltage controller 20D. The voltage controller 20D applies a prescribed voltage (bias voltage) to the bias wiring line 16 based on the control signal from the timing controller 20E.

The X-rays radiated from the X-ray light source 30 pass through the specimen S and enter the scintillator 10A. The X-rays that have entered the scintillator 10A are converted into scintillation light, and the scintillation light enters the imaging panel 10.

When the scintillation light enters the photodiode 15 disposed in the respective pixels 13 in the imaging panel 10, the photodiode 15 converts the scintillation light into an electric charge that corresponds to the intensity of the scintillation light.

The data signal that corresponds to the electric charge converted by the photodiode 15 passes through the data line 12 and is read out by the signal reader 20B when a gate voltage (plus voltage) received from the gate controller 20A via the gate line 11 turns ON the TFT 14. An X-ray image that corresponds to the read-out data signal is generated by the image processor 20C.

(Manufacturing Method of Imaging Panel 10)

Next, a method of manufacturing the imaging panel 10 will be explained. FIGS. 5 to 11 are cross-sectional views of the pixel 13 along lines A-A and B-B during each manufacturing step of the imaging panel 10.

Figure 5:
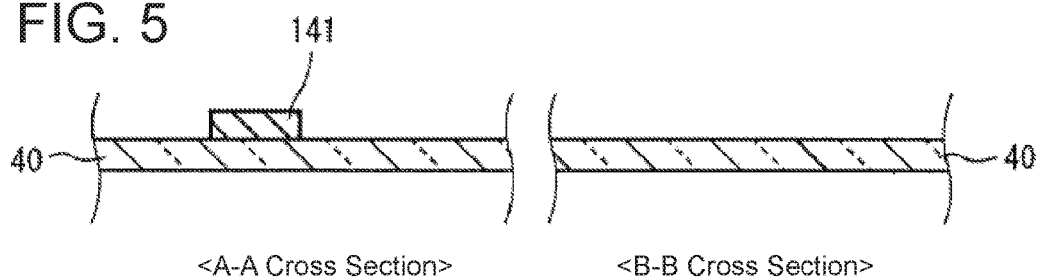
FIG. 5 is a cross-sectional view of a pixel in the manufacturing process of the gate electrode along the line A-A and along the line B-B.

As shown in FIG. 5, sputtering or the like is used to form an aluminum/titanium layered metal film on the substrate 40. Thereafter, photolithography is used to pattern this metal film to form the gate electrode 141 and gate line 11. The thickness of the metal film is 300 nm, for example.

Figure 6:
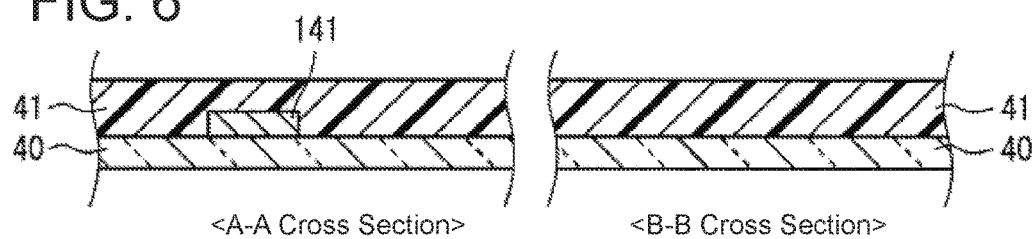
FIG. 6 is a cross-sectional view during a manufacturing process of a gate insulating film of the pixel shown in FIG. 3 along the line A-A and along the line B-B.

Next, as shown in FIG. 6, plasma-enhanced CVD or sputtering etc. is used to form the gate insulating film 41 made of silicon oxide (SiOx) or silicon nitride (SiNx) etc. on the substrate 40 so as to cover the gate electrode 141. The thickness of the gate insulating film 41 is 20 nm to 150 nm, for example.

Figure 7:
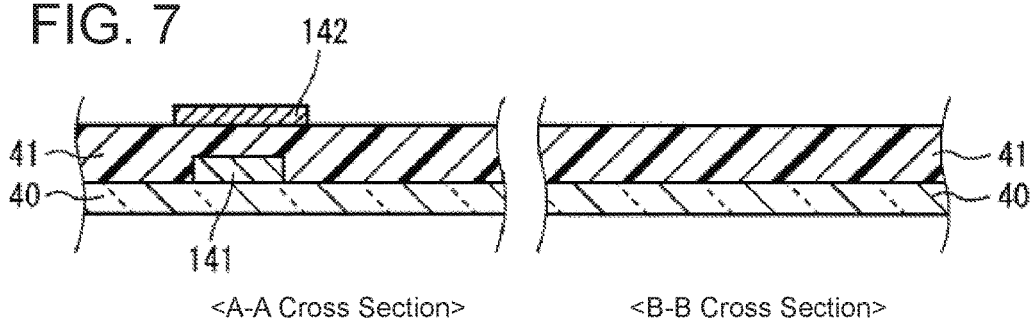
FIG. 7 is a cross-sectional view during a manufacturing process of a semiconductor active layer of the pixel shown in FIG. 3 along the line A-A and along the line B-B.

Next, as shown in FIG. 7, sputtering etc. is used to form an oxide semiconductor on the gate insulating film 41, and photolithography is used to pattern the oxide semiconductor to form the semiconductor active layer 142, for example. After the semiconductor active layer 142 has been formed, a high-temperature heat treatment (350° C. or greater, for example) is performed in an environment containing oxygen (e.g., the atmosphere). In such a case, it is possible to reduce oxygen defects in the semiconductor active layer 142. The thickness of the semiconductor active layer 142 is 30 nm to 100 nm, for example.

Figure 8:
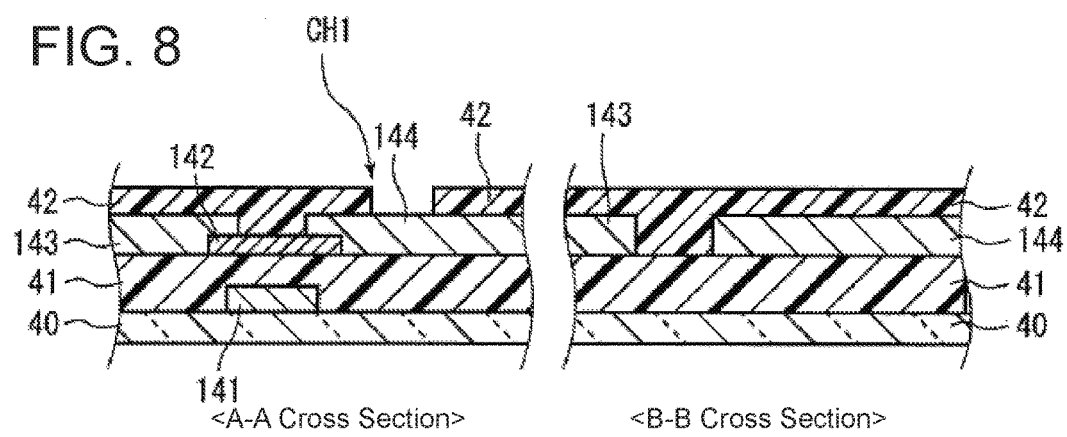
FIG. 8 is a cross-sectional view during a manufacturing process of a source electrode and a drain electrode of the pixel shown in FIG. 3 along the line A-A and along the line B-B.

Next, as shown in FIG. 8, sputtering or the like used to layer titanium, aluminum, and titanium metal films in this order on the gate insulating film 41 and semiconductor active layer 142. Thereafter, photolithography is used to pattern this metal film to form the source electrode 143, data line 12, and drain electrode 144. The thickness of the source electrode 143, data line 12, and drain electrode 144 is 50 nm to 500 nm, for example. The etching may be either dry etching or wet etching, with dry etching being suitable if the area of the substrate 40 is large. This forms a bottom-gate TFT 14.

Next, plasma-enhanced CVD is used to form the silicon oxide ($SiO_2$) or silicon nitride (SiN) interlayer insulating film 42 on the source electrode 143, data line 12, and drain electrode 144, for example. Thereafter, a thermal treatment of approximately 350° C. is performed on the entire surface of the substrate 40, and photolithography is used to pattern the interlayer insulating film 42 and form the contact hole CH1.

Next, as shown in FIG. 9, sputtering or the like is used to form the n-type amorphous silicon layer 151, intrinsic amorphous silicon layer 152, and p-type amorphous silicon layer 153 in this order on the interlayer insulating film 42 and the drain electrode 144. Thereafter, photolithography is used for patterning, and dry etching is performed to form the photodiode 15.

Next, sputtering or the like is used to deposit indium zinc oxide (IZO) on the interlayer insulating film 42 and photodiode 15, which is patterned by photolithography to form the electrode 43.

Next, as shown in FIG. 10, plasma-enhanced CVD or the like is used to deposit silicon oxide ($SiO_2$) or silicon nitride (SiN) on the interlayer insulating film 42 and electrode 43, and the interlayer insulating film 44 is formed. Thereafter, photolithography is used for patterning in order to form the contact hole CH2 on the electrode 43.

Next, as shown in FIG. 11, a photosensitive resin is deposited on the interlayer insulating film 44 and dried to form the photosensitive resin layer 45. Then, sputtering or the like is used to deposit indium tin oxide (IZO) and molybdenum (Mo) metal film layers on the photosensitive resin layer 45, and these are patterned by photolithography to form the bias wiring line 16.

In the embodiment described above, the bias line 16 is formed on the TFT 14 in each of the pixels 13, and thus it is possible to prevent degradation of the TFTs 14 caused by scintillation light and to inhibit shifting of the threshold voltage of the TFTs 14.

Furthermore, in each of the pixels 13, the bias wiring line 16 is disposed so as to overlap the edge portion 15E1 of the photodiode 15 near the data line 12 to which the TFT 14 is connected. In other words, the bias wiring line 16 is disposed closer to the data line 12 to which the TFT 14 is connected than the center in the extension direction of the gate line 11 on the photodiode 15. Therefore, it is possible to improve the aperture ratio of the pixel 13 as compared to if the bias wiring line 16 were disposed near the center in the extension direction of the gate line 11 on the photodiode 15.

If, in order to improve the aperture ratio, the photodiode 15 and drain electrode 144 are formed up to a position near the data line 12, the gap between the drain electrode 144 and the data line 12 narrows. The drain electrode 144 and the data line 12 are formed in the same layer, and thus, during manufacturing, the attachment of a particle larger than the gap between the drain electrode 144 and the data line 12 would cause a pattern defect in the drain electrode 144 and data line 12. In the embodiment described above, in the drain electrode 144 of the pixel 13, edge portions 144E1 and 144E2 of the drain electrode 144 in the extension direction of the gate line 11 and not connected to the semiconductor active layer 142 are more inside the pixel 13 than edge portions 15E1 and 15E2 of the photodiode 15 in the extension direction of the gate line 11. Thus, the aperture ratio of the pixel 13 can be maintained while enlarging the gap between the data line 12 and the drain electrode 144, as compared to if the photodiode 15 and drain electrode 144 were formed up to a position near the data line 12. As a result, during manufacturing, it is possible to reduce the occurrence of pattern defects caused by particles attaching to the space between the data line 12 and the drain electrode 144.

Modification Examples

An embodiment of the present invention has been described above, but the above embodiment is a mere example of an implementation of the present invention. Thus, the present invention is not limited to the embodiment described above, and can be implemented by appropriately modifying the embodiment described above without departing from the spirit of the present invention. Next, modification examples of the present invention will be explained.

Figure 12:
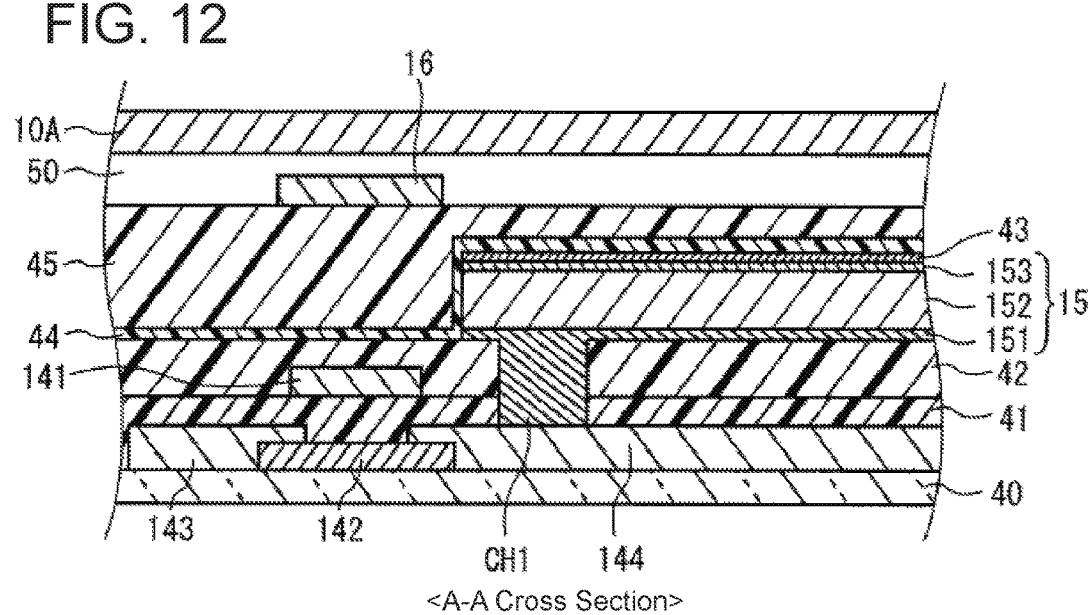
FIG. 12 is a cross-sectional view of a pixel of an imaging panel having a top-gate TFT according to Modification Example 1.
Figure 13:
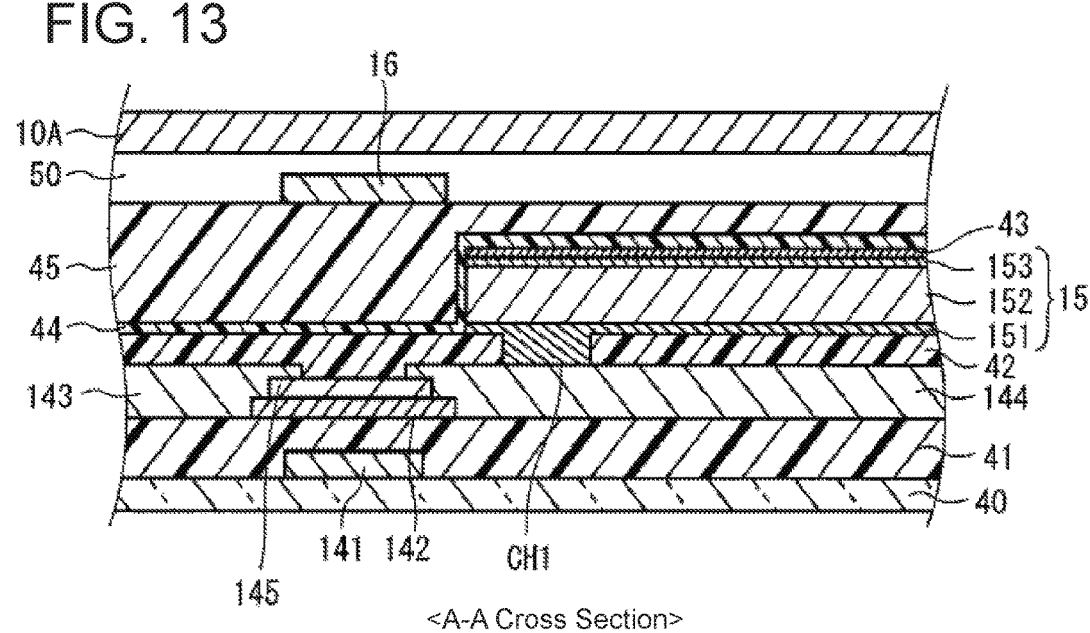
FIG. 13 is a cross-sectional view of the pixel of the imaging panel of Modification Example 1.

(1) In the embodiment described above, an example was described in which the imaging panel 10 has a bottom-gate TFT 14, but as shown in FIG. 12, the TFT 14 may be a top-gate TFT, or may be the bottom-gate TFT shown in FIG. 13, for example.

The parts that differ from the embodiment described above for the method of manufacturing an imaging panel having the top-gate TFT 14 shown in FIG. 12 will be explained below. First, the semiconductor active layer 142 made of an oxide semiconductor is formed on the substrate 40. Then, titanium, aluminum, and titanium are layered in this order on the substrate 40 and semiconductor active layer 142 to form the source electrode 143, data line 12, and drain electrode 144.

Next, the silicon oxide (SiOx) or silicon nitride (SiNx) etc. gate insulating film 41 is formed on the semiconductor active layer 142, source electrode 143, data line 12, and drain electrode 144. Thereafter, aluminum and titanium are layered on the gate insulating film 41 to form the gate electrode 141 and gate line 11.

After the gate electrode 141 is formed, the interlayer insulating film 42 is formed on the gate insulating film 41 so as to cover the gate electrode 141, and the contact hole CH1 is formed penetrating through to the drain electrode 144. Then, in a similar manner to the embodiment described above, the photodiode 15 is formed on the interlayer insulating film 42 and the drain electrode 144.

Furthermore, in the case of an imaging panel equipped with a TFT 14 having an etch stop layer 145 as shown in FIG. 13, then in the above-mentioned embodiment, after the semiconductor active layer 142 is formed, plasma-enhanced CVD or the like is used to deposit silicon oxide ($SiO_2$) on the semiconductor active layer 142, for example. Thereafter, photolithography is used to pattern and form the etch stop layer 145. Then, after the etch stop layer 145 is formed, titanium, aluminum, and titanium may be layered in this order on the semiconductor active layer 142 and the etch stop layer 145 to form the source electrode 143, data line 12, and drain electrode 144.

(2) In the embodiment described above, an example is described in which, in each of the pixels 13, the bias wiring line 16 overlaps the TFT 14. Taking into consideration the improvement of the aperture ratio of the pixel 13 and the prevention of degradation of the TFT 14 caused by light, it is desirable that the bias wiring line 16 indeed be disposed as in the embodiment described above, but the location of the bias wiring line 16 is not limited to this. In summary, the bias wiring line 16 may be electrically connected to the photodiode 15 in the pixel 13.

What is claimed is:

1. An imaging panel for capturing scintillation light that has been converted by a scintillator from X-rays radiated from an X-ray source, the imaging panel comprising:
   a substrate;
   a plurality of gate lines on the substrate;
   a plurality of data lines on the substrate and intersecting the plurality of gate lines;
   a plurality of conversion elements respectively disposed in a plurality of regions demarcated by the plurality of gate lines and the plurality of data lines, said plurality of conversion elements receiving the scintillation light and converting the scintillation light to electric charge; and
   thin film transistors respectively disposed in the plurality of regions and connected to the conversion element in the corresponding region and connected to the gate line and the data line contacting the corresponding region, each of the thin film transistors including a drain electrode in a same layer as the data line, and having a semiconductor active layer therein,
   wherein, in each of the plurality of regions, an edge of the drain electrode near the data line is more inside the corresponding region than an edge of the conversion element near the data line.

2. The imaging panel according to claim 1, wherein the semiconductor active layer is made of an oxide semiconductor.

3. The imaging panel according to claim 1, wherein the semiconductor active layer is amorphous silicon or polycrystalline silicon.

4. The imaging panel according to claim 1,
   wherein the thin film transistors each include:
      a gate electrode on the substrate;
      an insulating film covering the gate electrode; and
      a source electrode on the insulating film and connected to the semiconductor active layer, wherein the drain electrode is on the insulating film and connected to the semiconductor active layer, and wherein the semiconductor active layer is on the insulating film.

5. The imaging panel according to claim 1,
wherein the thin film transistors each include:
- a source electrode connected to the semiconductor active layer;
- an insulating film covering the semiconductor active layer, the source electrode, and the drain electrode; and
- a gate electrode on the insulating film, and wherein the drain electrode is connected to the semiconductor active layer.

6. An X-ray imaging device, comprising:
the imaging panel according to claim 1,
a controller controlling gate voltages of the thin film transistors in the imaging panel and reading out via the data lines data voltages that correspond to electric charge converted by the conversion elements;
an X-ray light source radiating X-rays; and
a scintillator converting the X-rays to scintillation light.

* * * * *